United States Patent
Baer et al.

(10) Patent No.: US 10,138,333 B2
(45) Date of Patent: Nov. 27, 2018

(54) PROCESS FOR PREPARING A BIO-RESORBABLE POLYESTER IN PARTICULATE FORM

(71) Applicant: Evonik Roehm GmbH, Darmstadt (DE)

(72) Inventors: Hans Baer, Michelstadt (DE); Christian Brunnengraeber, Lorsch (DE)

(73) Assignee: Evonik Roehm GmbH, Darmstadt (DE)

( * ) Notice: Subject to any disclaimer, the term of this patent is extended or adjusted under 35 U.S.C. 154(b) by 99 days.

(21) Appl. No.: 15/524,412

(22) PCT Filed: Nov. 9, 2015

(86) PCT No.: PCT/EP2015/076040
§ 371 (c)(1),
(2) Date: May 4, 2017

(87) PCT Pub. No.: WO2016/075071
PCT Pub. Date: May 19, 2016

(65) Prior Publication Data
US 2018/0282489 A1    Oct. 4, 2018

(30) Foreign Application Priority Data
Nov. 14, 2014 (EP) .................................. 14193199

(51) Int. Cl.
*C08J 3/12* (2006.01)
*C08J 3/14* (2006.01)
*A61K 47/34* (2017.01)
*A61L 31/14* (2006.01)
*A61L 31/06* (2006.01)
*A61L 27/18* (2006.01)
*A61L 27/58* (2006.01)
*B29L 31/00* (2006.01)
*B29C 47/00* (2006.01)
*B29K 67/00* (2006.01)

(52) U.S. Cl.
CPC .............. *C08J 3/12* (2013.01); *A61K 47/34* (2013.01); *A61L 27/18* (2013.01); *A61L 27/58* (2013.01); *A61L 31/06* (2013.01); *A61L 31/148* (2013.01); *C08J 3/14* (2013.01); *B29C 47/0066* (2013.01); *B29K 2067/04* (2013.01); *B29K 2995/006* (2013.01); *B29L 2031/7532* (2013.01); *C08J 2367/04* (2013.01)

(58) Field of Classification Search
CPC . C08J 3/12; C08J 3/14; C08J 2367/04; A61K 47/34; A61L 27/18; A61L 27/58; A61L 31/06; A61L 31/148; B29C 47/0066; B29K 2067/04; B29K 2995/006
USPC ........................................................... 428/402
See application file for complete search history.

(56) References Cited

FOREIGN PATENT DOCUMENTS

| EP | 2455414 | * | 5/2012 |
| EP | 2455414 A1 | | 5/2012 |
| WO | 2007/088135 | * | 8/2007 |
| WO | 2007/088135 A1 | | 8/2007 |
| WO | 2015/028060 | * | 3/2015 |
| WO | 2015/028060 A1 | | 3/2015 |

OTHER PUBLICATIONS

International Search Report and Written Opinion dated Jan. 12, 2016, in PCT/EP2015/076040 filed Nov. 9, 2015.
European Search Report dated Apr. 23, 2015, in European Patent Application No. 14193199.8 filed Nov. 14, 2014.

* cited by examiner

*Primary Examiner* — Leszek B Kiliman
(74) *Attorney, Agent, or Firm* — Grüneberg and Myers PLLC

(57) ABSTRACT

The invention refers to process for preparing a bio-resorbable polyester in particulate form, comprising the steps: a) providing a bio-resorbable polyester with in the form of a dry polymer mass or in the form of a wet polymer mass; b) feeding the polymer mass from step a) into an extruder with at least one degassing zone where the polymer mass is molten, extruded and degassed; c) discharging the degassed polymer mass out of the extruder; d) comminuting the discharged polymer mass to particles with —a bulk density of 0.3 g/ml or more, —a tapped density of 0.4 g/ml or more and —a specific surface area of 2.0 $m^2$/g or less.

16 Claims, No Drawings

PROCESS FOR PREPARING A BIO-RESORBABLE POLYESTER IN PARTICULATE FORM

TECHNICAL FIELD

The invention refers to a process for preparing a bio-resorbable polyester in particulate form with a specified bulk density, tapped density and surface area by means of extrusion and subsequent comminution.

TECHNICAL BACKGROUND

U.S. Pat. No. 4,810,775 describes a process for the purification of resorbable polyesters. U.S. Pat. No. 5,007,923 describes crystalline copolyesters of amorphous lactide/glycolide and dioxanone. U.S. Pat. No. 6,706,854 describes a process for preparing resorbable polyesters by mass polymerization. US2010/0137550A1 describes a method and device for cleaning absorptive or resorbable polyester. The process for purifying a resorbable polyester is comprising the steps of dissolving the resorbable polyester in a first solvent to form a polymer solution, intimately contacting the polymer solution with a second solvent under the action of high shear forces in a turbulent shear field to form a polymer suspension, wherein the second solvent is a non-solvent for the resorbable polyester and is unlimitedly miscible with the first solvent, conveying the polymer suspension onto or into a rotating cylindrical screen body and drying the polymer mass.

Problem and Solution

Bio-resorbable polyesters are well known in the art for preparing bio-degradable pharmaceutical active ingredient containing dosage forms suitable for in-situ sustained release applications in the human body or in an animal body. Bio-resorbable polyesters are also used for preparing bio-degradable surgical articles, such as filaments, rods, stents or prostheses. The preparation of controlled release articles or medical devices usually requires certain specification of bio-resorbable polyesters raw material which is usually delivered in particulate form, for instance in the form of a powder or granulate. Although several methods for preparing Bio-resorbable polyesters are known, it is often difficult to meet certain specifications. A general problem is the formation of microscopic pores in the material during the drying processes probably induced by evaporation of included gases especially water evaporation. Such pores are unwanted in the further processing. The inventors describe herein a process as claimed for preparing bio-resorbable polyesters in which existing microscopic pores or the formation of microscopic pores in the particulate material is remarkably reduced or totally avoided. This reduction of micropores is indicated by a high bulk density of 0.3 g/ml or more, a high tapped density of 0.4 g/ml or more and a low specific surface area of 2.0 $m^2$/g or less. This specification is beneficial since the further processing of the bio-resorbable polyesters for instance by injection molding to surgery articles such as stents or other implantable articles becomes more reproducible and reliable. The amount of articles out of the specification in production processes can be reduced.

The problem is solved by a process for preparing a bio-resorbable polyester in particulate form,
comprising the steps
a) providing a bio-resorbable polyester with in the form of a dry polymer mass or in the form of a wet polymer mass,
b) feeding the polymer mass from step a) into an extruder extruder with at least one degassing zone where the polymer mass is molten, extruded and degassed
c) discharging the degassed polymer mass out of the extruder
d) comminuting the discharged polymer mass to particles with
a bulk density of 0.3 g/ml or more,
a tapped density of 0.4 g/ml or more and
a specific surface area of 2.0 $m^2$/g or less It was by no means to be foreseen that this particular specification could be achieved by the process as described herein.

Definitions and Analytical Methods

Bulk/Tapped Density

The determinations of the bulk/tapped density are performed according to the United States Pharmacopeia 36 (USP) chapter <616> and European Pharmacopeia (EP) chapter 2.9.15. The interparticulate interactions that influence the bulk properties of a powder are also the interactions that interfere with the powder flow, a comparison of the bulk and tapped densities can give a measure of the relative importance of these interactions in a given powder. The bulk density of the powder "as poured" or passively filled into a measuring vessel. The tapped density is a limiting density attained after "tapping down," usually in a device that lifts and drops a volumetric measuring cylinder containing the powder a fixed distance.

Bulk Density

The bulk density is determined by measuring the volume of a known mass of powder sample that has been passed without agglomerates into a graduated cylinder (Method I) or through a volume-measuring apparatus into a cap (Method II). For the purposes of the described invention only Method I was utilized for bulk density determinations.

Tapped Density

The tapped density is achieved by mechanically tapping a measuring cylinder containing a powder sample. After observing the initial volume, the cylinder is mechanically tapped, and volume readings are taken until only a little volume change is observed. The mechanical tapping is achieved by raising the cylinder and allowing it to drop under its own weight a specified distance.

Specific Surface Area

The determination of the specific surface area is preferably performed according to the United States Pharmacopeia 36 (USP) chapter <846> and European Pharmacopeia 7.0 (EP) chapter 2.9.26. The specific surface area is determined utilizing a specific surface area detection equipment (e.g. Quantachrome Nova 2000e BET).

Inherent Viscosity (IV)

The determination of the inherent viscosity is preferably performed in a Ubbelohde viscometer of type 0c at 25±0.1° C. utilizing a sample concentration of 0.1% dissolved in chloroform.

Water Content Determination

The water content may be determined coulometric by the Karl Fischer method or gravimetric by the loss on drying method.

Karl Fischer Method/Coulometric Titration

The determination of the water content may be performed according to the United States Pharmacopeia 36 (USP) chapter <921> Method Ic and European Pharmacopeia 7.0 (EP) chapter 2.5.32. The Karl Fischer (KF) reaction is used in the coulometric determination of water. Iodine, however, is not added in the form of a volumetric solution but is produced in an iodide-containing solution by anodic oxidation. In the KF oven method, the test substance is heated in a tightly sealed vessel in an oven. The water driven off from the sample is transported into the titration cell with the help of a stream of dry nitrogen gas; there it is determined, usually by means of coulometric KF titration. As reference a standard lactose samples are utilized. Because the sample itself remains in the vessel and only the water enters the titration cell, secondary reactions and matrix effects can be ruled out.

Gravimetric/Loss on Drying (LOD)

The water content may be performed may be determined according to the United States Pharmacopeia 36 (USP) chapter <921> Method III and procedure for chemicals—proceed as directed in the individual monograph preparing the chemical as directed under Loss on Drying (LOD) <731> and also according European Pharmacopeia 7.0 (EP) chapter 2.2.32. However, this method suffers from the drawback that it determines not only the water content, but also other volatile constituents in the sample.

Thermal Analysis

The thermal analysis may be performed may be determined according to the United States Pharmacopeia 36 (USP) chapter <891> and European Pharmacopeia 7.0 (EP) chapter 2.2.34.

$T_{v,0,1}$=Temperature at a decomposition rate of 0.1%/K $T_{0,peak\ 1}$=Decomposition temperature species 1

$T_{0,peak\ 2}$=Decomposition temperature species 2

Table 1 summarizes the different decomposition temperatures of a number of widely used bio-resorbable polyesters of the poly(D,L-lactide) and poly(D,L-lactide-co-glycolide) type which are commercially available under the Trade name RESOMER®.

Particle Size Distribution

The particle size may be determined by light diffraction (laser scattering) or by image analysis.

Specific Surface Area

The specific surface area is preferably determined according to the United States Pharmacopeia 36 (USP) chapter <846> and European Pharmacopeia 7.0 (EP) chapter 2.9.26. The specific surface area is determined utilizing a specific surface area detection equipment (e.g. Quantachrome Nova 2000e BET). The specific surface area was measured using the multi-point and single-point determination using the static-volumetric method (Method II). Prior to the measurement the sample is degassed at 20° C. and vacuum is applied.

Inherent Viscosity IV

The Inherent viscosity (IV) is preferably determined in an Ubbelohde viscometer of type 0c at 25±0.1° C. utilizing a sample concentration of 0.1% dissolved in chloroform.

Glass Transition Temperatures

The different Glass transition temperatures are preferably determined according to the United States Pharmacopeia 36 (USP) chapter <891>, European Pharmacopeia 7.0 (EP) chapter 2.2.34 and according to DIN 53765:1994-03 (D).

$T_g$=glass transition temperature $T_{gO}$=glass transition onset temperature $T_{gO}^E$=glass transition extrapolated onset temperature $T_{gE}$=Glass transition end temperature $T_{gE}^E$=Glass transition extrapolated end temperature Glass Transition Temperatures of Bio-Resorbable Polyesters Table 2 summarizes the different glass transition temperatures of a number of widely used bio-resorbable polyesters of the poly(D,L-lactide) and poly(D,L-lactide-co-glycolide) type which are commercially available under the Trade name RESOMER®.

TABLE 1

Decomposition Temperatures of Bio-resorbable Polyesters of the poly(D,L-lactide) and poly(D,L-lactide-co-glycolide) type

| RESOMER ® | Polymer Composition | IV (dL/g) | Tv0.1 [° C.] | $T_{0,\ peak\ 1}$ [° C.] | $T_{0,\ peak\ 2}$ [° C.] |
|---|---|---|---|---|---|
| RG 502 H | Poly(D,L-lactide-co-glycolide) 50:50 | 0.20 | 172 | 271 | 335 |
| RG 504 H | Poly(D,L-lactide-co-glycolide) 50:50 | 0.59 | 186 | 276 | 311 |
| RG 752 H | Poly(D,L-lactide-co-glycolide) 75:25 | 0.20 | 220 | 357 | n/a |

TABLE 2

Glass Transition Temperatures of Bio-resorbable Polyesters of the poly(D,L-lactide) and poly(D,L-lactide-co-glycolide) type

| RESOMER ® | Polymer Composition | IV (dL/g) | End group | $T_{gO}$ [° C.] | $T_{gO}^{E}$ [° C.] | $T_{g}$ [° C.] | $T_{gE}^{E}$ [° C.] | $T_{gE}$ [° C.] |
|---|---|---|---|---|---|---|---|---|
| R 202 S | Poly(D,L-lactide) | 0.22 | Ester | 34.3 | 37.8 | 40.3 | 43.2 | 48.3 |
| R 202 H | Poly(D,L-lactide) | 0.23 | Acid | 44.0 | 47.0 | 48.8 | 50.5 | 55.4 |
| R 203 S | Poly(D,L-lactide) | 0.32 | Ester | 39.1 | 44.0 | 46.2 | 48.5 | 54.4 |
| R 203 H | Poly(D,L-lactide) | 0.33 | Acid | 46.1 | 48.9 | 50.5 | 52.1 | 57.5 |
| RG 502 | Poly(D,L-lactide-co-glycolide) 50:50 | 0.22 | Ester | 36.6 | 39.7 | 41.4 | 43.1 | 48.2 |
| RG 502 H | Poly(D,L-lactide-co-glycolide) 50:50 | 0.20 | Acid | 38.2 | 42.6 | 44.1 | 45.7 | 51.2 |
| RG 503 | Poly(D,L-lactide-co-glycolide) 50:50 | 0.43 | Ester | 41.8 | 44.9 | 46.5 | 48.1 | 53.2 |
| RG 503 H | Poly(D,L-lactide-co-glycolide) 50:50 | 0.35 | Acid | 40.6 | 44.9 | 46.6 | 48.3 | 54.6 |
| RG 504 | Poly(D,L-lactide-co-glycolide) 50:50 | 0.59 | Ester | 41.9 | 46.1 | 48.1 | 50.0 | 56.2 |
| RG 504 H | Poly(D,L-lactide-co-glycolide) 50:50 | 0.59 | Acid | 41.1 | 45.6 | 47.6 | 49.6 | 56.2 |
| RG 653 H | Poly(D,L-lactide-co-glycolide) 65:35 | 0.37 | Acid | 39.2 | 45.9 | 47.8 | 49.8 | 57.0 |
| RG 752 H | Poly(D,L-lactide-co-glycolide) 75:25 | 0.20 | Acid | 38.8 | 44.1 | 46.0 | 48.0 | 53.8 |
| RG 752 S | Poly(D,L-lactide-co-glycolide) 75:25 | 0.19 | Ester | 31.0 | 33.9 | 36.5 | 39.1 | 44.7 |
| RG 750 S | Poly(D,L-lactide-co-glycolide) 75:25 | 1.11 | Ester | 45.8 | 49.3 | 51.1 | 52.9 | 59.1 |

Bio-Resorbable Polyester

A bio-resorbable polyester in the sense of the invention is preferably a lactic acid polymer or a lactic acid based polymer in a broad sense, for instance a homopolymer or copolymer based for instance on lactide (L-lactide, D-lactide, DL-lactide, mesolactide), glycolide, epsilon caprolactone, dioxanone, trimethylene carbonate, delta-valerolactone, gamma-butyrolactone and similar polymerizable heterocycles. These polymers can either be composed of one or else of a plurality of different monomer modules in the polymer chain such as for instance ethylene glycol. Bio-resorbable polyesters are raw materials which are widely used for the production of bio-resorbable surgical implants and also as a pharmaceutical carrier for the formulation of parenteral release systems.

The bio-resorbable polyester can be a polylactic acid, a polyglycolic acid, a poly-caprolactone, a lactic acid-glycolic acid copolymer, a lactic acid-glycolic acid-polyethylene block copolymer, a lactic acid-glycolic acid-caprolactone terpolymer, a lactic acid-caprolactone copolymer, a poly dioxanone or a lactic acid-trimethylene carbonate copolymer or any blend of the fore mentioned polymers.

The bio-resorbable polyester is preferably selected from lactic acid polymers or copolymers synthesized from monomer components or from a mixture of monomer components selected from the group consisting of a) to l):

a) D- and L-lactide,
b) L-lactide and glycolide,
c) D,L-lactide and glycolide,
d) L-lactide and epsilon-caprolactone,
e) L-lactide and dioxanone,
f) L-lactide and trimethylene carbonate,
g) L-lactide, D-lactide, meso-lactide or D,L-lactide,
h) L-lactide,
i) DL-lactide,
j) statistically distributed monomer units of L-lactide, D-lactide, meso-lactide or DL-lactide and epsilon caprolactone,
k) statistically distributed monomer units of L-lactide, D-lactide, meso-lactide or DL-lactide and dioxanone,
l) statistically distributed monomer units of L-lactide, D-lactide, meso-lactide or DL-lactide and trimethylene carbonate.

These kind of lactic acid polymers or copolymers are biodegradable polyester polymers and well known in the art for example from EP1468035, U.S. Pat. No. 6,706,854, WO2007/009919A2, EP1907023A, EP2263707A, EP2147036, EP0427185 or U.S. Pat. No. 5,610,266. Depending on the production process the polymers may have different end groups such as ester or acid end groups.

Preferably the bio-resorbable polyester is a poly(D,L-lactide-co-glycolide) copolymer preferably with an inherent viscosity IV from 0.1-2.0, 0.12-1.2, 0.14-1.0, 0.16-0.44, 0.16-0.24 [dL/g].

A preferred bio-resorbable polyester is a poly(D,L-lactide-co-glycolide) copolymer with a proportion of D,L-lactide:glycolide in the poly(D,L-lactide-co-glycolide) copolymer from 80:20 to 20:80, 70:30 to 30:70, 60:40 to 40:60 or 80:20 to 60:40 parts by weight, where the parts D,L-lactide:glycolide add up to 100%.

Preferred bio-resorbable polyester are of the type of RESOMER® RG 502 or RESOMER® RG 502 H which are a poly(D,L-lactide-co-glycolide)-copolymers with a D,L-lactide:glycolide ratio of 45:55 to 55:45, preferred 50:50) and with an inherent viscosity IV in the range of 0.16-0.44 or 0.16-0.24 [dL/g].

The bio-resorbable polyester may be characterized by a glass transition temperature $T_g$ from about 30 to 60, 35 to 55° C.

The term "bio-resorbable" in "bio-resorbable polyester" means that the polyester, which is preferably a lactid acid based polymer, is after implantation or injection in the human body or in the body of an animal in contact with the body fluids broken down into oligomers in a slow hydrolytic reaction. Hydrolysis end products such as lactic acid or glycolic acid are metabolized into carbon dioxide and water. Other exchangeable expressions for the term "bio-resorbable polyester" which are often used are "resorbable polyester", "bio-degradable polyester" or "adsorptive polyester".

DETAILED DESCRIPTION OF THE INVENTION

The invention refers to a process for preparing a bio-resorbable polyester in particulate form, preferably in the form of a granulate or in the form of a powder, with a bulk density of 0.3 g/ml or more, 0.35 g/ml or more, 0.4 g/ml or more, 0.45 g/ml or more, 0.5 g/ml or more, preferably from 0.3 to 0.75, 0.35 to 0.65, 0.4 to 0.6, 0.4-0.45, 0.5-0.6 g/ml.

The invention refers to a process for preparing a bio-resorbable polyester in particulate form, preferably in the form of a granulate or in the form of a powder, with a tapped density of 0.4 g/ml or more, 0.5 g/ml or more, preferably from 0.4 to 0.75, 0.45 to 0.65, 0.5 to 0.55, 0.55-0.7 g/ml.

The invention refers to a process for preparing a bio-resorbable polyester in particulate form, preferably in the form of a granulate or in the form of a powder, with a specific surface area (BET, BET method) of 2.0 $m^2/g$ or less, 1.5 $m^2/g$ or less, 1.0 $m^2/g$ or less, 0.01-2 $m^2/g$, 0.1-1 $m^2/g$.

The Process Comprises the Steps a to d

Step a:

A bio-resorbable polyester is provided in the form of a dry polymer mass or in the form of a wet polymer mass.

Dry Polymer Mass

The bio-resorbable polyester may be provided as dry polymer mass in the form of a powder or a granulate preferably with a bulk density of less than 0.3, 0.05 to less than 0.3, 0.1-0.25 g/ml, a tapped density of less than 0.4, 0.1 to less than 0.4, 0.15-0.3 g/ml and a specific surface area of more than 2.0, 2.0-25, 2.5 to 15, 10-25 $m^2/g$.

Such a dry polymer mass is for instance available after the polymerization process of a bio-resorbable polyester, when the wet polymer mass is dried in a process employing a fluidized bed dryer. The dry polymer mass may have, before the extrusion process as described herein, a water content in the range of 0.2-2, 0.25-1 or 0.3-0.8% w/w (Karl Fischer method (KF)).

Wet Polymer Mass

A wet polymer mass is available after the polymerization process of the bio-resorbable polyester. After polymerization the bio-resorbable polyester is further processed by being dissolved in a first solvent which results in a polymer solution. The first solvent is preferably an organic solvent, for instance hexane, acetone, dioxan, dimethylacetamide, tetra-hydrofuran, toluol, dimethylformamide, dimethylsulfoxide or chlorinated hydrocarbons, such as chloroform or methlene chloride, or any mixtures thereof. Preferably the first solvent does not contain water or it may contain water only in small amounts of less than 1.0% (w/w), or in ranges of 0-0.5, 0.01-0.25% (w/w). For this purpose the bio-resorbable polyester may be already provided as a solution in such a first solvent. Alternatively the bio-resorbable polyester may be provided in solid form as a dry polymer mass and then be dissolved in the first solvent to form the polymer solution.

The polymer solution may be then contacted with a second solvent which is a non-solvent for the bio-resorbable polyester and which is or comprises water, preferably mainly water, to result the precipitation of the bio-resorbable polyester in the form of a wet polymer mass. Mainly water shall mean that the second solvent comprises at least 95% (w/w) or more, 98% or more, 99% or more water to which small amounts up to 5% (w/w) or less, 2% or less, 1% or less of processing auxiliaries, such as inorganic or organic acids, inorganic or organic bases, organic solvents like isopropanol or acetone, agents for varying the surface tension or complexing agents may be added. Preferably the second solvent is (100%) water. Most of the second solvent in excess may be removed by filtration. After filtration a wet or aqueous polymer mass remains. The wet polymer mass may still show a residual water content of around 50% or more, 60% or more, 70% or more, 80% or more, 90% or more, 50-90%, 60-80% by weight/weight (w/w). The wet polymer mass may usually have the form of a lump, a clot or a nugget. The terms "comprises water" or "comprises mainly water" shall mean that the second solvent is either 100% water, or a mixture of more than 50, more than 60, more than 70, more than 80 or more than 90% water with water soluble solvents such as acetone, ethanol or isopropanol. Preferably the second solvent is water.

Step b):

In step b) the polymer mass, which may be a dry polymer mass or a wet polymer mass, from step a) is fed into an extruder with at least one degassing zone. In the extruder the polymer mass is molten, extruded and degassed, whereby included gases or volatile substances respectively water is removed as water vapour in the one or more degassing zones to result in a degassed polymer mass with water content of 1% or less, 0.8% or less or 0.5% or less, 0.3% or less by weight/weight (measured as loss on drying (LOD)).

The extruder is preferably a double screw extruder.

The extruder is preferably a double screw extruder with counter rotating barrels.

An extruder which may be used in step b) has usually different temperatures zones, maybe five to 12 temperature zones, and one or more degassing zones. The feeding zone is usually the first temperature zone at the beginning of the extruder and has usually the lowest temperature, for instance cooled to 10-15° C. In this zone the polymer mass is fed and conveyed to the second zone, the first heating zone. The second zone is heated for instance to 45-60° C. Then the temperature and the pressure increases in the course of the next temperature zones, for instance to 80, then to 100 and then to 120° C. In these zones the polymer mass is kneaded and mixed by the rotating extruder screws, the melt viscosity decreases and high pressure is built up. One or more degassing zones are usually following downstream to these high temperature and high pressure zones. In the one or more degassing zones volatile substances, like water, are removed under negative pressure from the polymer melt. At the very end of the extruder the molten polymer mass or polymer melt is run off, preferably as a polymer strand, and thereby discharged and allowed to cool down. The water content is reduced remarkably. If the water content should be still too high, the discharged polymer mass may be extruded and thereby degassed once again in the same or in another extruder.

The melt temperature in the extruder should be high enough to provide a polymer melt viscosity low enough to allow the polymer mass to be processed by the extruder forces. On the other hand the melt temperature should be low enough to avoid thermic degradation of the bio-degradable polyester. The polymer mass in step c may be extruded at temperature of the polymer melt in the range of about 80 to 170, 90 to 150, 95 to 130° C. Such a temperature shall be present in at least in one of the different temperature zones of the extruder, preferably in a temperature zone directly before the one or more degassing zones.

The melt pressure may be in the range of 10 to 100, 20 to 80 bar at the extruder die. The pressure in the one or more degassing zones of the extruder may be characterized by a negative pressure of minus 100 to minus 900, minus 100 to minus 500, minus 200 to minus 400 mbar.

The mass throughput of the polymer mass through the extruder may be from about 0.1 to 10, 0.2 to 5, 0.5 to 2.5 kg/h. A typical speed of the extruder barrel or barrels may be in the range of about 100 to 200 rpm.

Step c):

In step c) the degassed polymer mass is run off, discharged or taken out of the extruder preferably as a polymer strand. The discharged polymer mass may leave the extruder as a polymer strand which is still in warm and elastic form and is then allowed to cool down. The discharged polymer strand may go over a conveying belt and may be cooled by compressed air flushing the conveying belt. The conveying belt may be positioned directly after the discharging outlet at the end opposite to the feeding zone of the extruder.

Step d):

In step d) the discharged polymer mass is comminuted to a granulate or to a powder. Preferably the discharged polymer mass is first comminuted to a granulate and then the granulate is further comminuted to a powder. It may also be possible to comminute the discharged mass in one step directly to a powder.

The discharged polymer mass may be comminuted, preferably in strand form, cut to a granulate by a granulator equipment. Such granulator equipment may be positioned directly after the conveying belt at the end opposite to the feeding zone of the extruder. The granulate particles may be of a cylindrical shape with a diameter in a range from about 1 to 5, 1.5-3 mm and a length in a range from about 0.5 to 50, 1-20 mm.

Comminution to a powder may be performed by a powder mill, preferably a jet mill avoiding too much energy uptake of the bio-resorbable polyester to temperatures above the $T_{gO}$. The powder particles are usually of a regular spherical shape.

Such a powder may preferably have a particle size with a $d_{50}$ of 1 to 300 µm and a $d_{90}$ of more than 30 and up to 3000, $d_{50}$ of 10 to 100 µm and $d_{90}$ of more than 50 and up to 1000 µm or less, $d_{50}$ of 1 to 30 and $d_{90}$ of more than 30 and up to 60 µm. The $d_{10}$ value is preferably less than 100, less than 10, for instance 1 to less than 10 µm.

Bio-Resorbable Polyester

The process according to the invention provides a bio-resorbable polyester in particulate form, preferably in the form of a granulate or in the form of a powder, preferably with a particle size with a $d_{50}$ of 1 to 300 µm and $d_{90}$ of more than 30 and up to 3000, $d_{50}$ of 10 to 100 µm and $d_{90}$ of more than 50 and up to 1000 µm or less, $d_{50}$ of 1 to 30 and $d_{90}$ of more than 30 and up to 60 µm. The $d_{10}$ value may be less than 100, less than 10, for instance 1 to less than 10 µm. A preferred bio-resorbable polyester is a lactic acid polymer including copolymers or a polylactic acid.

The $d_{10}$ value is always lower than the $d_{50}$ value. The $d_{50}$ value is always lower than the $d_{90}$ value. Thus the $d_{10}$, the $d_{50}$ and $d_{90}$ ranges mentioned here are allowed to overlap without being partially identical, illogical or illegitimate since in every case of a particle distribution the $d_{10}$ value is lower than the $d_{50}$ value and the $d_{50}$ value is lower than the $d_{90}$ value. In the case of an overlapping of the $d_{50}$ and $d_{90}$ ranges, the $d_{50}$ value is lower than the $d_{90}$ value. In the case of an overlapping of the $d_{10}$ the $d_{50}$ or the $d_{90}$ ranges, the $d_{10}$ value is lower than the $d_{50}$ value and the $d_{50}$ value is lower than the $d_{90}$ value.

Thus a bio-resorbable polyester in the form of a powder with a mean particle size $d_{50}$ of 1-300 µm and $d_{90}$ of more than 30-1000 µm, a bulk density of less 0.3 g/ml or more, a tapped density of 0.4 g/ml or more and a specific surface area of 2.0 m²/g or less is obtainable from the process as disclosed herein.

Use

The bio-resorbable polyester may be used for preparing a bio-resorbable pharmaceutical active ingredient containing dosage form suitable for an in-situ sustained release application in the human body or in an animal body.

The bio-resorbable polyester may be used for preparing a bio-resorbable surgical article, such as filament, a rod, a stent or a prostheses.

EXAMPLES

Bulk Density

The bulk density was determined according to the United States Pharmacopeia 36 (USP) chapter <616> and European Pharmacopeia (EP) chapter 2.9.15 by measuring the volume of a known mass of powder sample that has been passed without agglomerates into a graduated cylinder (Method I).

Into a 100 ml (readable to 1 mm) cylinder, without compacting, an apparent volume between 50 ml and 100 ml is introduced, weighted [M] with 0.1% accuracy. Carefully the powder sample leveled without compacting, if necessary, and the apparent unsettled volume [$V_0$] is read to the nearest graduated unit. The bulk density is calculated in gram per milliliter [g/ml], by the formula:

$$\rho_{bulk} = \frac{M}{V_0}$$

Tapped Density

The Tapped density was determined according to the United States Pharmacopeia 36 (USP) chapter <616> and European Pharmacopeia (EP) chapter 2.9.15 by mechanically tapping a measuring cylinder containing a powder sample.

Into a 100 ml (readable to 1 mm) cylinder, without compacting, an apparent volume between 50 ml and 100 ml is introduced, weighted [M] with 0.1% accuracy. Carefully the powder sample leveled without compacting, if necessary, and the apparent unsettled volume [$V_0$] is read to the nearest graduated unit.

The cylinder was mechanically tapped containing the sample by raising the cylinder and allowing it to drop under its own weight using a suitable tapped density tester (e.g. JV1000; Fa. Copley) that provides a fixed drop of 3 mm±10% at a nominal rate of 250 drops per minute. The cylinder was initially tapped 500 times and the tapped volume [$V_a$] was measured to the nearest graduated unit. The tapping was repeated for an additional 750 times and the tapped volume [$V_b$] was measured to the nearest graduated unit. If the difference has to be incrementally repeated of 1250 taps, as needed, until the volume difference between succeeding measurements is less than 2%. This final tapped volume [$V_{tapped}$] was considered for the calculation of the tapped density. The tapped density was calculated in gram per milliliter [g/ml], by the formula:

$$\rho_{tapped} = \frac{M}{V_{tapped}}$$

Specific Surface Area

The determination of the specific surface area was performed according to the United States Pharmacopeia 36 (USP) chapter <846> and European Pharmacopeia 7.0 (EP) chapter 2.9.26. The specific surface area is determined utilizing a specific surface area detection equipment (e.g. Quantachrome Nova 2000e BET).

The specific surface area of a powder sample is determined by physical adsorption of a gas (e.g. nitrogen) on the surface of the solid and by calculating the amount of adsorbed gas corresponding to a monomolecular layer on the surface. Physical adsorption results from relatively weak forces (van der Waals forces) between the adsorbed gas molecules and the adsorbent surface of the test powder. The determination is usually carried out at the temperature of liquid nitrogen. The amount of gas adsorbed can be measured by a volumetric or continuous flow procedure.

The specific surface area was measured using the multi-point and single-point determination using the static-volumetric method (Method II).

Prior to the measurement the sample was degassed at 20° C. and vacuum was applied.

Thermal Analysis

The thermal analysis may be performed may be determined according to the United States Pharmacopeia 36 (USP) chapter <891> and European Pharmacopeia 7.0 (EP) chapter 2.2.34. The thermal analysis performed in accordance with the thermogravimetry analysis (TGA) method. The samples were not conditioned but stored at 5° C.±3° C. before thermal analysis. The sample weight monitoring started with measurement start. The TGA measurements started at ambient temperature (22° C.±3° C.) and were stopped at 505° C. with a heat rate of 5K/min.

Particle Size-/Particle Size Distribution-Measurement

Light Diffraction

The determination of the particle size was performed according to the United States Pharmacopeia 36 (USP) chapter <429> and European Pharmacopeia 7.0 (EP) chapter 2.9.31. The particle size distribution was determined utilizing a laser scattering instrument (e.g. Fa. Sympatec GmbH, type HELOS equipped with RODOS dry dispersing unit). The laser diffraction method is based on the phenomenon that particles scatter light in all directions with an intensity pattern that is dependent on particle size. A representative sample, dispersed at an adequate concentration in a suitable liquid or gas, is passed through the beam of a monochromic light source usually from a laser. The light scattered by the particles at various angles is measured by a multi-element detector, and numerical values relating to the scattering pattern are then recorded for subsequent analysis. The numerical scattering values are then transformed, using an appropriate optical model and mathematical procedure, to yield the proportion of total volume to a discrete number of size classes forming a volumetric particle size distribution (e.g. $d_{50}$ describes a particle diameter corresponding to 50% of cumulative undersize distribution).

Dry samples were transferred into aerosols through the use of powder dispersers, which apply mechanical forces for deagglomeration. The dosing device feeds the disperser with a constant mass flow of sample. The disperser utilizes the energy of compressed gas (e.g. 2 bar) or the differential pressure to a vacuum (e.g. 90-100 mbar) to disperse the particles. The required precision of the method is dependent on characteristics of the sample material (milled versus non-milled, robust vs. fragile). Appropriate measurement conditions are experimentally established, in relation to the desired precision. At least a triplicate detection of representative samples was conducted. The repeatability of the particle size distribution parameter was as follows: for any central value of the distribution (e.g. median $d_{50}$) the coefficient of variation was less than 10%. For values away from the median, (e.g. $d_{10}$ and $d_{90}$) the coefficient of variation did not exceed 15%. Below a particle size of 10 μm the coefficient of variation was doubled.

Particle Size Distribution/Image Analysis

Alternatively, to the laser diffraction method a dynamic image analysis was utilized after qualification with referencing to the light diffraction method. The basic concept is the combination of dry dispersing unit with dynamic image analysis (Fa. Sympatec GmbH, type QICPIC equipped with RODOS/L dry dispersing unit). A representative sample is dry dispersed and the particle flow is led through the image plane. Due to the dispersion the particles are separated from each other by the transportation fluid and overlapping particles are widely avoided.

Dry samples were transferred into aerosols through the use of powder dispersers, which apply mechanical forces for deagglomeration. The dosing device feeds the disperser with a constant mass flow of sample. The disperser utilizes the energy of compressed gas (e.g. 1 bar) or the differential pressure to a vacuum (e.g. 90-100 mbar) to disperse the particles. The required precision of the method is dependent on characteristics of the sample material (milled versus non-milled, robust vs. fragile). Appropriate measurement conditions were experimentally established, in relation to the desired precision. At least a triplicate detection of representative samples was conducted. The repeatability of the particle size distribution parameter was as follows: for any central value of the distribution (e.g. median $d_{50}$) the coefficient of variation was less than 10%. For values away from the median, (e.g. $d_{10}$ and $d_{90}$) the coefficient of variation does not exceed 15%. Below a particle size of 10 μm the coefficient of variation was doubled.

The samples are analyzed using a range module for the DIA sensor of 5-1.705 μm. The calculation of the measured data was performed utilizing the minimum Ferret diameter and "EQPC" mode of the Sympatec QX program package. "EQPC" is the diameter of a circle that has the same area as the projection area of the analyzed particle. The Ferret diameter in general is defined as the distance between the two tangents perpendicular to a particular measuring direction.

Water Content Determination a. Karl Fischer method/Coulometric Titration

The determination of the water content was performed according to the United States Pharmacopeia 36 (USP) chapter <921> Method Ic and European Pharmacopeia 7.0 (EP) chapter 2.5.32. The Karl Fischer (KF) reaction is used in the coulometric determination of water. Iodine, however, is not added in the form of a volumetric solution but is produced in an iodide-containing solution by anodic oxidation. In the KF oven method, the test substance is heated in a tightly sealed vessel in an oven. The water driven off from the sample is transported into the titration cell with the help of a stream of dry nitrogen gas; there it is determined, usually by means of coulometric KF titration. As reference a standard lactose samples are utilized. Because the sample itself remains in the vessel and only the water enters the titration cell, secondary reactions and matrix effects can be ruled out.

The following determination parameters were utilized for the coulometric KF titration. The blank value was determined in triplicate. The reference was determined with 100-150 mg lactose standard (e.g. Apura Lactose-Standard von Merck, Darmstadt, Art.-Nr. 1.12939). The sample was determined in duplicate with an amount of 0.5-0.6 mg. The oven temperature was adjusted to 150° C., if PEG-Copolymers were determined to 125° C. The nitrogen flow was adjusted at 50-70 ml/min.

The respective number of vials were open conditioned for at least 10 minutes. The vials for system set up and blank value were sealed before the reference samples were weighted into vials and sealed. The prepared vials should not be stored longer than 72 hours. The sample detection was performed according to the equipment manual (e.g. Fa. Methrom KF-Coulometer 756, Fa Metrohm KF-Oven Sample Processor with nitrogen connection, Fa Metrohm Dosino 700 and Fa Metrohm Magnetic Stirrer 728).

The analysis of the coulometric detected water content uitilized the following equation:

Blank Value $$B = W_B - \left(\frac{Z}{60 \cdot K}\right)$$

B=Blank Value [μg]
K=Drift at the end of the conditioner [μg/min]
$W_B$=Water mass of blank without drift [μg]
Z=Titration time [sec]

Standard Deviation $$SD = \frac{W_S \cdot 100}{S}$$

$W_S$=Determined water content of lactose standard
S=Supplier certified water content lactose standard Water Content $$W_{[\%]} = \frac{\left(W_S - \left(\frac{Z}{60 \cdot K}\right) - B\right) \cdot 100}{10000 \cdot E}$$

$$W_{[ppm]} = \frac{\left(W_S - \left(\frac{Z}{60 \cdot K}\right) - B\right) \cdot 100}{E}$$

W=Water content
$W_S$=Water mass of blank without drift [μg]
Z=Titration time [sec]
E=Weighted sample [g]
B=Blank Value [μg]

The average water content was calculated as average of the duplicate determination. The water content values are expressed herein as % by weight/weight (w/w)

a. Gravimetric/Loss on Drying (LOD)

The water content was determined according to the United States Pharmacopeia 36 (USP) chapter <921> Method III and procedure for chemicals—proceed as directed in the individual monograph preparing the chemical as directed under Loss on Drying (LOD) <731> and also according European Pharmacopeia 7.0 (EP) chapter 2.2.32. However, this method suffers from the drawback that it determines not only the water content, but also other volatile constituents in the sample The detection of the water content via gravimetric method was performed with a halogen moisture analyzer (e.g. Fa. Mettler Toledo, Type HG63). This kind of equipment is working according to the thermo-gravimetric principle. That means the water content is analyzed via the surrogate parameter of detected weight loss while heating a water containing sample.

At the beginning of the detection the sample was placed on an aluminum bowl and the net weight of the sample was detected considering the tare weight of the aluminum bowl. If the sample shows a mean particle size more than 2 mm the sample should be crushed, however, avoiding too much energy uptake of the sample to avoid water loss during the sample preparation. The required sample weight depends on the desired deviation of the reproducibility (Table 3).

TABLE 3

| Measurement Reproducibility | |
|---|---|
| Reproducibility of Results | Minimum sample Weight |
| ±0.02% | 10 g |
| ±0.05% | 4 g |
| ±0.1% | 2 g |
| ±0.2% | 1 g |

Then, the sample was be heated up to 110° C. and kept at this temperature during the detection period utilizing the halogen heating module of the halogen moisture analyzer. The moisture will volatile and the precision balance will detect a sample weight loss. The sample was dried until a constant mass was observed as predefined by a sample weight loss of less than 1 mg per 50 sec (e.g. Fa. Mettler Toledo, Type HG63; switch off criteria 3).

The analysis of the gravimetric detected water content utilized the following equation:

$$MC = \frac{m_w - m_D}{m_w} \cdot 100$$

$$DC = \frac{m_D}{m_w} \cdot 100$$

MC=Content of volatile constituents [%]
DC=Dry content [%]
$m_w$=Wet sample mass [g]
$m_d$=Dry sample mass [g]

The water content values are expressed herein as % by weight/weight (w/w)

Inherent Viscosity (IV)

The determination of the inherent viscosity was performed in a Ubbelohde viscometer of type 0c at 25±0.1° C. utilizing a sample concentration of 0.1% dissolved in chloroform. The inherent viscosity represents the ratio of the natural logarithm of the relative viscosity [$\eta_r$] to the mass concentration of the polymer [c]. The quantity [$\eta_{ln}$] with which the inherent viscosity is synonymous is the logarithmic viscosity number.

$$\eta_{IV} \equiv \eta_{ln} = \frac{\ln \eta_r}{c}$$

100±5 mg sample was introduced into a 100 ml graduated flask. The graduated flask was filled with approximately 9/10 chloroform and a ferrite stir bar was immersed. The sample was dissolved while stirring with the ferrite stir bar utilizing a rotating magnetic field (magnetic stirrer). The ferrite stir bar rotation speed was appropriately adjusted with regard to the stir bar dimensions and the sample characteristics. Samples with an expected IV of not more than 1 dl/g were stirred for at least 6 hours and samples with an expected IV equal or more than 1 dl/g were stirred for at least 12 hours to ensure the dissolution of the samples in chloroform. After the respective stirring period the ferrite stir bar was removed, the graduated flask was filled to the calibration mark with chloroform and the stir bar was immersed again. Afterwards, the sample was stirred for additional 15 minutes to ensure homogeneity of the sample.

In order to determine the down time of the Uppelohde viscometer filtrated chloroform was introduced into a clear and dry viscometer. The maximum volume (approximately 15 ml) is indicated by a mark. The determination of the down time was conducted with a triplicate determination of the retention time.

In order to determine the retention time of the sample the prepared and filtrated sample solution was introduced into the clean and dried Uppelohde viscometer. The determination of the filtrated sample solution was conducted in a triplicate. Samples with an expected IV not more than 0.24 dl/g were determined in different Uppelohde viscometers (e.g. 2 samples solution=4 single determinations=4 viscometer) in order to avoid outlier. The determined retention times equipment related was corrected according to the "Hagenbach" correction for DIN-viscometer (DIN 51562 part 3).

$$t = \frac{x}{Z^2}$$

$$x = \frac{2.49}{K \cdot \sqrt{K \cdot \frac{\sqrt[4]{(K*16.37375)}}{10}}}$$

For estimating the "Hagenbach" correction the following equation could be utilized with sufficient precision.

$$t = \frac{E}{K \cdot Z^2}$$

$$E = \frac{C}{K^{\frac{5}{8}}}$$

t=time correction [sec]
Z=average retention time [sec]
K=capillary constant of the utilized viscometer
C=5.59576 (for micro capillary 0.2331655)
The calculation of the IV the following equation will be utilized:

$$IV = \frac{\ln\frac{T}{T_0}}{c} = \frac{\ln\frac{Z_{sample} - t_{sample}}{Z_{solvent} - t_{solvent}}}{c}$$

IV=inherent viscosity [dl/g]
T=corrected sample retention time [sec]
$Z_{sample}$=retention time sample [sec]
$t_{sample}$=time correction [sec]
$T_0$=corrected solvent retention time [sec]
$Z_{solvent}$=retention time solvent [sec]
$t_{solvent}$=time correction solvent [sec]
c=concentration sample solution Glass Transition Temperature/Differential Scanning Calorimetry (DSC)

The different glass transition temperatures was determined according to the United States Pharmacopeia 36 (USP) chapter <891>, European Pharmacopeia 7.0 (EP) chapter 2.2.34 and more specific to DIN 53765:1994-03 (D).

DIN 53765:1994-03 (D) is defining the glass transition temperature more in detail: The glass transition is a reversible transition from a hard and relatively brittle, frozen state to a molten or rather rubbery state within amorphous or partly amorphous materials.

During the glass transition, numerous material properties as Young's modulus, specific heat capacity and the coefficient of thermal expansion are changing considerably faster (escalades) in comparison to the temperature range below and above.

The glass transition temperature is determined utilizing a Differential Scanning calorimeter (e.g. Fa. Netzsch; type DSC 200 PC). The aluminum sample pan (e.g. 25/40 µl) with perforated lid considering are tarred before approximately 5 mg sample are introduced. Afterward, the aluminum pan and lid are cold sealed. The first heating circle is introduced with a heat rate of 10K/min starting at 20° C. up to 150° C. under nitrogen atmosphere. Afterwards, the sample is cooled to −20° C. with a cooling rate of 10K/min before the second heating circle is started with a heating rate of 10K/min up to 150° C. The cooling temperature before the second heating cycle should be 50K below the expected glass transition temperature. The glass transition temperature is determined in the second heating run. Possibly observed peaks in the first heating circle are considered as relaxation peaks and, therefore, are not evaluated such peaks disappear in the second heating circle.

The temperature range where the glass transition occurs is defined as glass transition range. The glass transition is characterized utilizing the glass transition temperature ($T_g$) at which 50% of the change in specific heat capacity is reached. For further characterization of the glass transition range the following temperatures are also defined:

The glass transition onset temperature ($T_{gO}$) and the glass transition extrapolated onset temperature ($T_{gO}^E$)

The Glass transition end temperature ($T_{gE}$) and the glass transition extrapolated end temperature ($T_{gE}^E$)

The difference ΔT between the glass transition extrapolated onset temperature ($T_{gO}^E$) and glass transition Extrapolated End temperature ($T_{gE}^E$) is also defined.

Acid Value

The determination of the acid value is conducted utilizing potentiometric titration with tetra-n-butylammonium hydroxide (TBAH) solution, c=0.1 mol/l via dynamic equivalence point titration (DET). The sample will dissolved in 60 ml of a solvent mixture of 73% v/v chloroform (quality pro analysis [p.A.]), 13.5% v/v dioxan (quality p.A.) and 13.5% v/v methanol (quality p.A.) while gentle stirring for a maximum of 30 minutes. For samples with an expected acid value lower than 1 mg KOH/g an amount of 1.5-3 g is introduced into the solvent mixture and for samples with an expected acid value of more than 1 mg KOH/g an amount of 1.0-3 g is introduced into the solvent mixture considering a minimum consumption of 0.3 ml TBAH. The determination is conducted in the solvent mixture via potentiometric titration of the acid protons with TBAH. Before determining the sample solution the titer and the blank value of the solvent mixture is determined in duplicate. Afterwards, the sample will be determined at least in duplicate and the mean acid value is calculated.

The analysis of the acid value utilizes the following equation: 1 ml TBAH solution (c=0.1 mol/l) is equal to 5.611 mg KOH/g sample weight.

$$SZ = \frac{(V_P - V_{BL}) \cdot T \cdot M_{KOH}}{E_P}$$

SZ=acid value [mg KOH/g]
$V_P$=consumption TBAH [ml]
$V_{BL}$=consumption TBAH for blank value [ml]
T=titer TBAH
$M_{KOH}$=molar weight KOH (g/mol)
$E_P$=sample weight (g)

EXAMPLES

Structure of the Examples

Inventive Examples 1 to 10

The inventive examples 1 to 10 can be distributed into three groups.

Group 1

For the inventive examples 1 and 2 the bio-resorbable polyester (RESOMER® RG 502 H) was provided in the form of a wet polymer mass and then further processed according to steps b) to d). In step d) a powder material was produced and the bulk density, tapped density and specific surface area (only for inventive example 1, table 21) were specified.

Group 2:

For the inventive examples 3 and 4 the bio-resorbable polyester was provided as the commercially available dry polymer mass (RESOMER® RG 502 H) in the form of a powder as starting material for step a) and then further processed according to steps b) to d). In step d) a powder material was produced and the bulk density and tapped density was specified. In contrast to the dry polymer material gained by the inventive examples the commercially available dry polymer mass starting material originated from a process in which it was dried by a fluidized bed dryer (ca. 20-25° C.), which is different from step b) as described.

Group 3:

The inventive examples 5 to 10 were merely performed to investigate minimum melt temperature conditions for step b). In the inventive examples 5 to 10 the bio-resorbable polyester (RESOMER® RG 502 H) used was again provided as the commercially available dry polymer mass in the form of a powder as a starting material in step a) and was then further processed according to steps b) to d) to a granulate without further specifying the bulk density, tapped density and specific surface area.

Comparative Examples C1 to C4

For the comparative examples C1 to C4 the investigated bio-resorbable polyester (RESOMER® RG 502 H) was again provided as the commercially available dry polymer mass in the form of a powder. In contrast, to the inventive examples 1 to 10 the commercially available dry polymer originated from a different drying process, where the polymer material was dried in a fluidized bed dryer with dry air (ca. 20-25° C.), which is different from step b) as described. This commercially available polymer material without any further processing was directly compared to the polymer material gained from the inventive examples 1-4.

Description of the Examples

A bio-resorbable polymer a Poly(D,L-lactide-co-glycolide) 50:50 with an inherent viscosity of approximately 0.2 and an acid end group (RESOMER® RG 502 H) was used in inventive examples 1 to 10 and in the comparative examples C1 to C4.

Inventive Examples 1 and 2

For inventive examples 1 and 2 the polymer was provided as wet polymer mass (step a). After polymerization the polymer was dissolved in acetone and then precipitated by the addition of an excess of water to form an aqueous polymer suspension. The aqueous polymer suspension was then mechanically pressed in order to reduce excess water to gain a wet polymer mass. The water content of the wet polymer mass was around 90% (w/w). The form of the wet polymer mass may be described as a lump, clot or nugget.

The wet polymer mass was extruded (step b) to remove the water as vapour and generate a degassed polymer mass with a residual water content 0.5% w/w. For this purpose the wet polymer mass was fed into the extruder, which was equipped with a feeding zone, 7 heating zones and a die. The screws may be set up as detailed in table 15 below. The extruder was further equipped with a degassing unit in order to remove water from the wet polymer mass. The extruded polymer mass was discharged out of the extruder (step c) as a polymer strand. The polymer strand was cooled via a compressed air cooled conveying belt before it was cut in a granulator. In the case that the remaining water content exceeded a value of 0.5% w/w (LOD) a second extrusion cycle was conducted to achieve a water content ≤0.5% w/w.

Subsequently, the polymer granules were filled into a jet mill (step d). The milling process was carried out with compressed air or optional with nitrogen. The final milled powder material was collected in a polyethylene bag behind a cyclone filter.

The polymer particles of example 1 were milled utilizing a jet mill to a powder with a particle size distribution of $d_{50}$ of 23.5 µm and $d_{90}$ of 36.6 µm (step d).

In example 2 milling was performed with a hammer mill to a powder with a particle size distribution of $d_{50}$ of 134.0 µm and $d_{90}$ of 258.4 µm (third milling step).

Inventive Examples 3 and 4

Inventive examples 3 and 4 were carried out in the same way as inventive examples 1 and 2 with the exception that a different starting material in step a) was used and the milling in step d) was modified. The starting material originated from the same process from which the wet polymer mass was gained however the polymer was additionally dried in a fluidized bed dryer equipment at ca. 20-25° C. inlet air temperature. Thus the starting material for step a) in inventive examples 3 and 4 was a dry polymer mass.

Furthermore, for inventive examples 3 and 4 milling was performed with a Retsch ZM 200 rotor stator mill utilizing screens of 0.5 mm and 1 mm, respectively.

Particle size distribution in inventive example 3 was $d_{50}$=99.5 µm and $d_{90}$ of 226.5 µm or $d_{50}$=141.4 µm and $d_{90}$ of 403.7 µm respectively.

Particle size distribution in inventive example 4 was $d_{50}$=122.6 µm and $d_{90}$ of 259.5 µm or $d_{50}$=146.6 µm and $d_{90}$ of 382.4 µm respectively.

Inventive Examples 5 to 10

Inventive examples 5 to 10 were carried out in the same way as inventive examples 3 and 4 with the exception that no milling in step d) was carried out. The starting material for step a) was therefore a dry polymer mass which was comminuted to granules in step d) as only the extrusion process was monitored to investigate the minimum melt temperature suitable to adjust during an extrusion process performed with the described set up.

Comparative Examples C1 to C4

The polymer material used in comparative examples C1 to C4 were four batches of the starting material (dry polymer mass in the form of a powder) for step a) in the inventive examples 3 to 10. No further processing of that material was performed.

Inventive Example 1

TABLE 4

Melt Extrusion
Batch: Inventive Example 1
Doser 1: RESOMER ® RG 502 H
Diameter of the die: 2.0 mm
Extruder: Leistritz MICRO 18 GL 40 D Pharma with degassing unit

| Extruder parameter: | Set up | Actual values | Inventive Example 1 cycle 1 | Inventive Example 1 cycle 2 | LOD |
|---|---|---|---|---|---|
| temperature cylinder 1 (° C.) | 50 | melt temperature cylinder 4 (° C.) | 100 | 105 | Inventive Example 1 cycle 1 (step b) |
| temperature cylinder 2 (° C.) | 80 | melt temperature cylinder 5 (° C.) | 105 | 115 | 1.33% w/w after the first extrusion cycle |
| temperature cylinder 3 (° C.) | 100 | melt temperature cylinder 6 (° C.) | 83 | 90 | |
| temperature cylinder 4 (° C.) | 110 | screw speed extruder (rpm) | 145 | 150 | Inventive Example 1 cycle 2 (step b) |
| temperature cylinder 5 (° C.) | 110 | current drive power (kW) | 1.0 | 1.8 | 0.19% w/w after the second extrusion cycle |
| temperature cylinder 6 (° C.) | 105 | melt pressure (bar) | 33 | 60 | |
| temperature cylinder 7 (° C.) | 85 | degassing depression (mbar) | −600 | −600 | Inventive Example 1 (step d) |
| temperature die (° C.) | 85 | throughput (kg/h) | manual | 1.00 | 0.23% w/w after milling |

TABLE 5

Jet Milling
Batch: Inventive Example 1 (step d)
Doser RESOMER ® RG 502 H
Jet Mill Hosokawa Alpine Jet Mill AFG 100
Milling Parameters

| | | | |
|---|---|---|---|
| Nozzle [mm] | 1.9 | Throughput [kg/h] | 2.05 |
| Classifier | Standard | Time [min] | 80 |
| Classifier speed [rpm] | 3,600 | Pressure [bar] | 6.0 |

TABLE 6

Results Particle Size Distribution

| Batch | $d_{10}$ | $d_{50}$ | $d_{90}$ |
|---|---|---|---|
| Inventive Example 1 | 7.06 μm | 23.45 μm | 36.61 μm |

TABLE 7

Physicochemical Results

| Physical value | Specification | Value Comparative Example C1 | Value Inventive Example 1 |
|---|---|---|---|
| Appearance (Color) | white to off-white | white to off-white | white to off-white |
| Appearance | solid | solid | solid |
| Odor | almost smell free | almost smell free | almost smell free |
| Identity | reference | reference | reference |
| Composition D,L-Lactid | 48-52 mol-% | 50.0 mol-% | 50.70 mol-% |
| Composition Glycolid | 48-52 mol-% | 50.0 mol-% | 49.30 mol-% |
| Inherent Viscosity | 0.16-0.24 dl/g | 0.21 dl/g | 0.20 dl/g |
| Water Content (Karl Fischer Method) | ≤0.5% (w/w) | 0.13% (w/w) | 0.09% (w/w) |
| Acid Value | ≥6 mg KOH/g | 9.50 mg KOH/g | 10.2 mg KOH/g |
| Bulk Density | ≥0.3 g/ml | 0.07 g/ml | 0.40 g/ml |
| Tapped Density | ≥0.4 g/ml | 0.10 g/ml | 0.56 g/ml |
| Glass Transition Temperature [Tg] | 38-50° C. | n/a | 43.6° C. |

Result:

Inventive example 1 demonstrates that the wet polymer mass could be dried by an melt extrusion process and milled with a jet mill without significant degradation of the investigated Poly(D,L-lactide-co-glycolide) 50:50. The relevant product specification of specified commercial Poly(D,L-lactide-co-glycolide) 50:50 are confirmed and the results of inventive example 1 are comparable to that of comparative example C1. The process leads to optimized product characteristics, especially for bulk and tapped density as well as for the resulting specific surface area (s. table 21).

Inventive Example 2

TABLE 8

Melt Extrusion
Batch: Inventive Example 2
Doser 1: RESOMER ® RG 502 H
Diameter of the die: 2.0 mm
Extruder: Leistritz MICRO 18 GL 40 D Pharma with degassing unit

| Extruder parameter: | Set up | Actual values | Inventive Example 2 cycle 1 | Inventive Example 2 cycle 2 | LOD |
|---|---|---|---|---|---|
| temperature cylinder 1 (° C.) | 80 | melt temperature cylinder 4 (° C.) | 96 | 105 | Inventive Example 2 |
| temperature cylinder 2 (° C.) | 100 | melt temperature cylinder 5 (° C.) | 99 | 111 | cycle 1 (step b) |
| temperature cylinder 3 (° C.) | 100 | melt temperature cylinder 6 (° C.) | 90 | 92 | 0.57% MC after the first extrusion cycle |
| temperature cylinder 4 (° C.) | 105 | screw speed extruder (rpm) | 100 | 100 | Inventive Example 2 |
| temperature cylinder 5 (° C.) | 110 | current drive power (kW) | 0.9 | 1.3 | cycle 2 (step b) |
| temperature cylinder 6 (° C.) | 105 | melt pressure (bar) | 30 | 21 | 0.23% MC after the second extrusion cycle |
| temperature cylinder 7 (° C.) | 90 | degassing depression (mbar) | −800 | −850 | Inventive Example 2 |
| temperature die (° C.) | 90 | throughput (kg/h) | manual | 0.7 | (step d) 0.41% MC after milling |

Milling (step d)

The milling are conducted with a HammerWitt-Lab (Fa. FREWITT) three milling steps required 1. 1×N° 459897 perforated plate Conidur 0.3 mm
2. 1×N° 453938 perforated plate 0.2 mm
3. 1×N° 440140, woven sieve 0.125×0.091 mm All steps conducted with 4000 rpm rotor speed

TABLE 9

Results Particle Size Distribution

| Batch: Inventive Example 2 | $d_{10}$ | $d_{50}$ | $d_{90}$ |
|---|---|---|---|
| Milling step 1 | 43.91 +/− 0.32 μm | 174.25 +/− 1.99 μm | 314.05 +/− 0.61 μm |
| Milling step 2 | 44.25 +/− 3.17 μm | 165.14 +/− 7.86 μm | 282.12 +/− 5.80 μm |
| Milling step 3 | 40.22 +/− 0.63 μm | 134.02 +/− 2.66 μm | 258.42 +/− 4.36 μm |

TABLE 10

Physicochemical Results

| Physical value | Specification | Value Comparative Example C2 | Value Inventive Example 2 |
|---|---|---|---|
| Appearance (Color) | white to off - white solid | white to off - white solid | white to off - white solid |
| Appearance | | | |
| Odor | almost smell free | almost smell free | almost smell free |
| Identity | reference | reference | reference |
| Composition D,L-Lactid | 48-52 mol-% | 50.5 mol-% | 51.0 mol-% |
| Composition Glycolid | 48-52 mol-% | 49.5 mol-% | 49.0 mol-% |
| Inherent Viscosity | 0.16-0.24 dl/g | 0.21 dl/g | 0.22 dl/g |
| Water Content (Karl Fischer Method) | ≤0.5% (w/w) | 0.15% (w/w) | 0.13% (w/w) |
| Acid Value | ≥6 mg KOH/g | 9.4 mg KOH/g | — |
| Bulk Density | ≥0.3 g/ml | 0.09 g/ml | 0.64 g/ml |
| Tapped Density | ≥0.4 g/ml | 0.12 g/ml | 0.83 g/ml |
| Glass Transition Temperature [Tg] | 38-50° C. | 44.0° C. | 43.0° C. |

Result:

Inventive example 2 demonstrates that the wet polymer mass could be dried by an melt extrusion process and milled with a hammer mill without significant degradation of the investigated Poly(D,L-lactide-co-glycolide) 50:50. The relevant product specification of specified commercial Poly(D,L-lactide-co-glycolide) 50:50 are confirmed and the results of inventive example 2 are comparable to the comparative example C2. The process leads to optimized product characteristics, especially for bulk and tapped density.

Inventive Example 3-4

TABLE 11

Melt Extrusion
Batch: Inventive Example 3 and 4
Doser 1: RESOMER ® RG 502 H
Diameter of the die: 1.5 mm
Extruder: Leistritz MICRO 18 GL 40 D Pharma with degassing unit

| Extruder parameter: | Set up | Actual values | Inventive Example 3 | Inventive Example 4 |
|---|---|---|---|---|
| temperature cylinder 1 (° C.) | 50 | melt temperature cylinder 4 (° C.) | 103 | 104 |
| temperature cylinder 2 (° C.) | 90 | melt temperature cylinder 5 (° C.) | 109 | 109 |
| temperature cylinder 3 (° C.) | 100 | melt temperature cylinder 6 (° C.) | 107 | 108 |
| temperature cylinder 4 (° C.) | 105 | screw speed extruder (rpm) | 140 | 152 |
| temperature cylinder 5 (° C.) | 110 | current drive power (kW) | 1.4 | 1.7 |
| temperature cylinder 6 (° C.) | 105 | melt pressure (bar) | 35 | 56 |
| temperature cylinder 7 (° C.) | 100 | throughput (kg/h) | 0.7 | 1.0 |
| temperature die (° C.) | 100 | | | |

Milling (Step d)

The milling was performed with a Retsch ZM 200 rotor stator mill utilizing screens of 0.5 mm and 1 mm.

TABLE 12

Results Particle Size Distribution

| Material | Evaluation Mode | d10 [μm] | d50 [μm] | d90 [μm] |
|---|---|---|---|---|
| Comparative Example 3 | Ferret min | 31.75 | 64.06 | 227.97 |
| Inventive Example 3 (0.5 mm) | | 43.09 | 99.53 | 226.51 |
| Inventive Example 3 (1 mm) | | 47.34 | 141.40 | 403.71 |
| Comparative Example 4 | | 25.73 | 45.75 | 99.43 |
| Inventive Example 4 (0.5 mm) | | 47.28 | 122.64 | 259.53 |
| Inventive Example 4 (1 mm) | | 49.06 | 146.64 | 382.35 |

TABLE 13

Physicochemical Results

| Physical value | Specification | Value Comparative Example C3 | Value Inventive Example 3 (0.5 mm) | Value Inventive Example 3 (1 mm) |
|---|---|---|---|---|
| Appearance (Color) | white to off - white | white to off - white | white to off - white | white to off - white |
| Appearance | solid | solid | solid | solid |
| Odor | almost smell free | almost smell free | almost smell free | almost smell free |
| Identity | reference | reference | reference | reference |
| Composition D,L-Lactid | 48-52 mol-% | 51 mol-% | — | — |
| Composition Glycolid | 48-52 mol-% | 49 mol-% | — | — |
| Inherent Viscosity | 0.16-0.24 dl/g | 0.18 dl/g | 0.18 dl/g | 0.19 dl/g |
| Water Content (Karl Fischer Method) | ≤0.5% (w/w) | 0.20% (w/w) | 0.14% (w/w) | 0.13% (w/w) |
| Acid Value | ≥6 mg KOH/g | 11.5 mg KOH/g | n/a | n/a |
| Bulk Density | ≥0.3 g/ml | 0.18 g/ml | 0.55 g/ml | 0.56 g/ml |
| Tapped Density | ≥0.4 g/ml | 0.28 g/ml | 0.77 g/ml | 0.76 g/ml |
| Glass Transition Temperature [Tg] | 38-50° C. | 41° C. | 41° C. | 40° C. |
| Melt viscosity | — | 5.32 mNm/218 Pa s | 5.85 mNm/186 Pa s | — |

TABLE 14

Physicochemical Results

| Physical value | Specification | Value Comparative Example C4 | Value Inventive Example 4 (0.5 mm) | Value Inventive Example 4 (1 mm) |
| --- | --- | --- | --- | --- |
| Appearance (Color) | white to off - white | white to off - white | white to off - white | white to off - white |
| Appearance | solid | solid | solid | solid |
| Odor | almost smell free | almost smell free | almost smell free | almost smell free |
| Identity | reference | reference | reference | reference |
| Composition D,L-Lactid | 48-52 mol-% | 51 mol-% | — | — |
| Composition Glycolid | 48-52 mol-% | 49 mol-% | — | — |
| Inherent Viscosity | 0.16-0.24 dl/g | 0.22 dl/g | 0.22 dl/g | 0.21 dl/g |
| Water Content (Karl Fischer Method) | ≤0.5% (w/w) | 0.26% (w/w) | 0.17% (w/w) | 0.15% (w/w) |
| Acid Value | ≥6 mg KOH/g | 11.5 mg KOH/g | n/a | n/a |
| Bulk Density | ≥0.3 g/ml | 0.17 g/ml | 0.57 g/ml | 0.60 g/ml |
| Tapped Density | ≥0.4 g/ml | 0.26 g/ml | 0.82 g/ml | 0.80 g/ml |
| Glass Transition Temperature [Tg] | 38-50° C. | 42° C. | 42° C. | 41° C. |
| Melt viscosity | — | 10.25 mNm/420 Pa s | 9.91 mNm/406 Pa s | — |

Result:

Inventive example 3 and 4 demonstrate that also dry polymer mass could be processed with an melt extrusion process and milled without significant degradation of the investigated Poly(D,L-lactide-co-glycolide) 50:50. The relevant product specifications of specified commercial Poly (D,L-lactide-co-glycolide) 50:50 are confirmed and the results of inventive example 3 and 4 are comparable to the comparative examples C3 and C4. The process leads to optimized product characteristics, especially for bulk and tapped density.

Inventive Examples 5 to 10

With these inventive examples the minimum melt temperature for step b) was evaluated at the extruder cylinders equipped with melt temperature sensors. As extrusion system a co-rotating Leistritz MICRO 18 GL 40 D Pharma twin screw extruder with degassing unit was utilized. The Leistritz MICRO 18 GL 40 D Pharma was set up with a powder feeder, cooled feeding zone (10-20° C.), seven heating zones and a die (diameter 3 mm or 5 mm). Second to the feeding zone the first temperature zone at the beginning of the extruder was installed. In this zone the polymer mass began to melt. Then the temperature and the pressure increased in the course of the next temperature zones. In these zones the polymer mass is kneaded by the rotating extruder screws, the melt viscosity decreases and high pressure is built up. One degassing zones followed downstream to these high temperature and high pressure zones. At the very end of the extruder the molten polymer mass or polymer melt run off, as a polymer strand, and thereby discharged and allowed to cool down.

Inventive examples 5 to 10 indicated that the cylinder temperature for dry polymer mass RESOMER® RG 502H needs to be set to at least approximately 65° C. or more using the extrusion set up as described below. Switching of criteria of the below described extrusion set up is a current drive power of more than 2.2 kW. The drive of the extrusion unit will then automatically stop in order to protect the screws from damages in case exceeding the maximum applicable torque per screw of 20 Nm. Inventive examples 8 to 10 demonstrate that with a set cylinder temperature of 70° C. the capability of the equipment is nearly achieved. Therefore, the set up temperature for the cylinder should be preferably above 70° C. as demonstrated with inventive examples 5 to 7. In general, the melt temperature in the relevant cylinders equipped with melt temperature sensors could vary from the set up temperature of the relevant cylinders due to the value of mechanical energy during the extrusion process. Furthermore, for the evaluation of the minimum melt temperature the following screw design was utilized, different screw design may result in different minimum extrusion temperatures.

TABLE 15

Screw design

| Screw Length [mm] | Cylinder | Element Length [mm] | Element type |
| --- | --- | --- | --- |
| 90 | 1.0 | 90 | GFF 2-30-90 |
| 120 | 1.3 | 30 | GFA 2-20-30 |
| 150 | 1.7 | 30 | GFA 2-20-30 |
| 180 | 2.0 | 30 | GFA 2-20-30 |
| 210 | 2.3 | 30 | GFA 2-20-30 |
| 240 | 2.7 | 30 | GFA 2-15-30 |
| 270 | 3.0 | 30 | GFA 2-15-30 |
| 330 | 3.7 | 60 | GFM 2-15-60 |
| 390 | 4.3 | 60 | GFM 2-15-60 |
| 420 | 4.7 | 30 | GFA 2-15-30 |
| 450 | 5.0 | 30 | GFA 2-15-30 |
| 540 | 6.0 | 90 | GFA 2-30-90 |
| 570 | 6.3 | 30 | GFA 2-15-30 |
| 630 | 7.0 | 60 | GFA 2-15-60 |
| 660 | 7.3 | 30 | GFA 2-20-30 |
| 720 | 8.0 | 60 | GFA 2-30-60 |

*) GFF or GFA = co-rotating conveying elements
**) GFM = co-rotating combing mixing element

TABLE 16

Evaluation of Minimum Extrusion Temperature - Inventive Example 5
Minimum Extrusion Temperature
Doser 1: RESOMER ® RG 502 H
Diameter of the die: 3 mm
Extruder: Leistritz MICRO 18 GL 40 D Pharma with degassing unit

| Extruder parameter: | Set up | Actual values | Inventive Example 5 |
|---|---|---|---|
| temperature cylinder 1 (° C.) | 50 | melt temperature cylinder 4 (° C.) | 104 |
| temperature cylinder 2 (° C.) | 100 | melt temperature cylinder 5 (° C.) | 106 |
| temperature cylinder 3 (° C.) | 100 | melt temperature cylinder 6 (° C.) | 92 |
| temperature cylinder 4 (° C.) | 100 | screw speed extruder (rpm) | 120 |
| temperature cylinder 5 (° C.) | 100 | current drive power (kW) | 1.4 |
| temperature cylinder 6 (° C.) | 100 | melt pressure (bar) | 46 |
| temperature cylinder 7 (° C.) | 100 | throughput (kg/h) | 0.5 |
| temperature die (° C.) | 100 | | |

TABLE 17

Evaluation of Minimum Extrusion Temperature - Inventive Example 6
Minimum Extrusion Temperature
Doser 1: RESOMER ® RG 502 H
Diameter of the die: 3 mm
Extruder: Leistritz MICRO 18 GL 40 D Pharma with degassing unit

| Extruder parameter: | Set up | Actual values | Inventive Example 6 |
|---|---|---|---|
| temperature cylinder 1 (° C.) | 50 | melt temperature cylinder 4 (° C.) | 92 |
| temperature cylinder 2 (° C.) | 90 | melt temperature cylinder 5 (° C.) | 97 |
| temperature cylinder 3 (° C.) | 90 | melt temperature cylinder 6 (° C.) | 89 |
| temperature cylinder 4 (° C.) | 90 | screw speed extruder (rpm) | 120 |
| temperature cylinder 5 (° C.) | 90 | current drive power (kW) | 1.3 |
| temperature cylinder 6 (° C.) | 90 | melt pressure (bar) | 14 |
| temperature cylinder 7 (° C.) | 90 | throughput (kg/h) | 0.5 |
| temperature die (° C.) | 90 | | |

TABLE 18

Evaluation of Minimum Extrusion Temperature - Inventive Example 7
Minimum Extrusion Temperature
Doser 1: RESOMER ® RG 502 H
Diameter of the die: 3 mm
Extruder: Leistritz MICRO 18 GL 40 D Pharma with degassing unit

| Extruder parameter: | Set up | Actual values | Inventive Example 7 |
|---|---|---|---|
| temperature cylinder 1 (° C.) | 50 | melt temperature cylinder 4 (° C.) | 82 |
| temperature cylinder 2 (° C.) | 80 | melt temperature cylinder 5 (° C.) | 84 |
| temperature cylinder 3 (° C.) | 80 | melt temperature cylinder 6 (° C.) | 81 |
| temperature cylinder 4 (° C.) | 80 | screw speed extruder (rpm) | 120 |
| temperature cylinder 5 (° C.) | 80 | current drive power (kW) | 1.9 |
| temperature cylinder 6 (° C.) | 80 | melt pressure (bar) | 23 |
| temperature cylinder 7 (° C.) | 80 | throughput (kg/h) | 0.5 |
| temperature die (° C.) | 80 | | |

TABLE 19

Evaluation of Minimum Extrusion Temperature - Inventive Examples 8 to 10
Minimum Extrusion Temperature
Doser 1: RESOMER ® RG 502 H
Diameter of the die: 3 or 5 mm
Extruder: Leistritz MICRO 18 GL 40 D Pharma with degassing unit

| Extruder parameter: | Set up | Actual values | Inventive Example 8 | Inventive Example 9 | Inventive Example 10 |
|---|---|---|---|---|---|
| temperature cylinder 1 (° C.) | 50 | melt temperature cylinder 4 (° C.) | 75 | 76 | 75 |
| temperature cylinder 2 (° C.) | 70 | melt temperature cylinder 5 (° C.) | 78 | 77 | 76 |
| temperature cylinder 3 (° C.) | 70 | melt temperature cylinder 6 (° C.) | 77 | 74 | 75 |
| temperature cylinder 4 (° C.) | 70 | screw speed extruder (rpm) | 120 | 120 | 110 |

TABLE 19-continued

Evaluation of Minimum Extrusion Temperature - Inventive Examples 8 to 10
Minimum Extrusion Temperature
Doser 1: RESOMER ® RG 502 H
Diameter of the die: 3 or 5 mm
Extruder: Leistritz MICRO 18 GL 40 D Pharma with degassing unit

| Extruder parameter: | Set up | Actual values | Inventive Example 8 | Inventive Example 9 | Inventive Example 10 |
|---|---|---|---|---|---|
| temperature cylinder 5 (° C.) | 70 | current drive power (kW) | 2.1 | 2.1 | 2.1 |
| temperature cylinder 6 (° C.) | 70 | melt pressure (bar) | 30 | 58 | 13 |
| temperature cylinder 7 (° C.) | 70 | throughput (kg/h) | 0.5 | 0.350 | 0.350 |
| temperature die (° C.) | 70 | die diameter (mm) | 3.0 | 3.0 | 5.0 |

Storage Stability

The powder material of inventive example 1 and comparative example C2 were stored in 100 ml HDPE bottles with LDPE caps. For each pull point a separate bottle was stored at 30° C. and ambient air humidity (approximately 50% relative humidity).

In tables 20 to 21 the storage stability was compared to the powder material from inventive example 1 and comparative example C2.

TABLE 20

Storage Stability of Comparative Example C2

| Comparative Example C2 | Storage | Acid value [mg KOH/g] | Inherent viscosity [dl/g] | Water content (KF) [% w/w] | BET*) [m$^2$/g] | Bulk density [g/ml] | Tapped density [g/ml] |
|---|---|---|---|---|---|---|---|
| Poly(D,L-lactide-co-glycolide) 50:50, acid end group | before storage | 9.6 | 0.22 | 0.38 | 13.058 | 0.09 | 0.12 |
| | 24 h/30° C. | 9.5 | 0.21 | 0.51 | 13.168 | n/a**) | n/a**) |
| | 48 h/30° C. | 9.4 | 0.21 | 0.67 | n/a**) | n/a**) | n/a**) |
| | 72 h/30° C. | 9.4 | 0.22 | 0.62 | n/a**) | n/a**) | n/a**) |
| | 96 h/30° C. | 9.4 | 0.21 | 0.46 | 6.449 | aggregated | aggregated |
| | 4 weeks/30° C. | 10.1 | 0.21 | 0.44 | 2.851 | aggregated | aggregated |

TABLE 21

Storage Stability of Inventive Example 1

| Inventive Example 1 | Storage | Acid value [mg KOH/g] | Inherent viscosity [dl/g] | Water content (KF) [% w/w] | BET*) [m$^2$/g] | Bulk density [g/ml] | Tapped density [g/ml] |
|---|---|---|---|---|---|---|---|
| Poly(D,L-lactide-co-glycolide) 50:50, acid end group | before storage | 10.2 | 0.21 | 0.12 | 0.436 | 0.45 | 0.57 |
| | 24 h/30° C. | 10.2 | 0.21 | 0.17 | 0.740 | n/a**) | n/a**) |
| | 48 h/30° C. | 10.2 | 0.22 | 0.21 | n/a**) | n/a**) | n/a**) |
| | 72 h/30° C. | 10.4 | 0.22 | 0.21 | n/a**) | n/a**) | n/a**) |
| | 96 h/30° C. | 10.4 | 0.21 | 0.24 | 0.334 | 0.46 | 0.57 |
| | 4 weeks/ 30° C. | 10.8 | 0.21 | 0.20 | 0.440 | 0.42 | 0.54 |

*)BET expresses the specific surface area (BET method)
**)Sample amount not sufficient for analysis Result: The powder material of comparative example C2 has an extremely high specific surface area and is less storage stable than powder material from inventive example 1. Surprisingly, the powder material of inventive example 1 does not show aggregation tendencies after 96 hours and 4 weeks storage at 30° C., respectively. Furthermore, the specific surface area of the powder material of inventive example 1 is rather stable as well as the bulk and tapped density. The specific surface area of comparative example C2 decreases significantly during the storage period of 4 weeks at 30° C. A smaller particle has a higher tendency to increase in size, and one of the ways of increasing in size is aggregation with a neighboring particle. Surprisingly, the powder material of comparative example C2 with the greater portion of large particles (Table 20) in comparison to inventive example 1 showed increased aggregation tendencies. Due to the lower specific surface the powder material of inventive example 1 is in a thermodynamic equilibrium avoiding aggregation at the applied storage conditions. The powder material from comparative example C2 shows a high surface area and is not in a thermodynamic equilibrium, which means the material starts to aggregate during the storage period at the applied storage conditions.

TABLE 22

Particle Size Comparison Inventive Example 1 and Comparative Example C2

| Batch | $d_{10}$ | $d_{50}$ | $d_{90}$ |
|---|---|---|---|
| Inventive Example 1 | 7.06 μm | 23.45 μm | 36.61 μm |
| Comparative Example C2 | 7.29 μm | 50.12 μm | 206.128 μm |

Therefore, the drying of wet polymer mass (inventive example 1) via extrusion improved significantly the powder material characteristics in comparison to currently available commercial material (comparative example C2). The extrusion and milling step produce material with lower specific surface areas, with higher bulk and tapped densities. Those material quality attributes, if stable over the shelf life, provide more reliable and stable material characteristics. Furthermore, production processes utilizing extruded and milled bio-resorbable polyesters do not need compensation of variable material qualities.

The invention claimed is:

1. A process for preparing a bio-resorbable polyester in particulate form, said process comprising:
    a) providing a bio-resorbable polyester in the form of a dry polymer mass or in the form of a wet polymer mass,
    b) feeding the polymer mass from a) into an extruder with at least one degassing zone where the polymer mass is molten, extruded and degassed, to obtain a degassed polymer,
    c) discharging the degassed polymer mass out of the extruder, and
    d) comminuting the discharged polymer mass to particles with
        a bulk density of 0.3 g/ml or more,
        a tapped density of 0.4 g/ml or more, and
        a specific surface area of 2.0 m²/g or less.

2. The process according to claim 1, wherein in a), the bio-resorbable polyester is provided as dry polymer mass in the form of a powder or a granulate with
    a bulk density of less than 0.3 g/ml,
    a tapped density of less than 0.4 g/ml, and
    a specific surface area of more than 2.0 m²/g.

3. The process according to claim 1, wherein in a), the bio-resorbable polyester is provided in the form of a wet polymer mass,
    wherein a bioresorbable polyester is dissolved in a first solvent or solvent mixture, and
    wherein the polymer solution is then contacted with a second solvent or solvent mixture which is a non-solvent for the bioresorbable polyester and which comprises at least 95% by weight of water to result the precipitation of the bio-resorbable polyester in the form of a wet polymer mass.

4. The process according to claim 3, whereby in c), the water of the wet polymer mass is removed in the one or more degassing zones of the extruder to result in a degassed polymer mass with water content of 1% or less by weight/weight.

5. The process according to claim 1, wherein the particles are a powder having a particle size of $d_{50}$ of 1-300 μm and $d_{90}$ of more than 30 and up to 3000 μm.

6. The process according to claim 1, wherein the polymer mass in c) is extruded at a melt temperature of the polymer melt in the range of about 80 to 170° C.

7. The process according to claim 1, wherein the pressure in the degassing zone of the extruder is a vacuum of minus 100 to minus 900 mbar.

8. The process according to claim 1, wherein the extruder is a double screw extruder.

9. The process according to claim 1, wherein the mass throughput of the extruded polymer mass through the extruder is from about 0.1 to 10 kg/h.

10. The process according to claim 1, wherein the bio-resorbable polyester is a polylactic acid, a polyglycolic acid, a poly-caprolactone, a lactic acid-glycolic acid copolymer, a lactic acid-glycolic acid-polyethylene block copolymer, a lactic acid-glycolic acid-caprolactone terpolymer, a lactic acid-caprolactone copolymer, a poly dioxanone, a lactic acid-trimethylene carbonate copolymer or a mixture thereof.

11. The process according to claim 1, wherein the bio-resorbable polyester is a poly(D,L-lactide-co-glycolide) copolymer with an inherent viscosity from 0.1-2.0.

12. The process according to claim 11, wherein the proportion of D,L-lactide to glycolide in the poly(D,L-lactide-co-glycolide) copolymer is from 70:30 to 30:70 parts by weight.

13. A bio-resorbable polyester obtainable from a process according to claim 1, which is in the form of a powder with
    a mean particle size $d_{50}$ of 1-300 μm,
    $d_{90}$ of more than 30 and up to 1000 μm,
    a bulk density of less 0.3 g/ml or more,
    a tapped density of 0.4 g/ml or more, and
    a specific surface area of 2.0 m²/g or less.

14. A bio-resorbable pharmaceutical active ingredient, comprising:
    the bio-resorbable polyester according to claim 13,
    a dosage form suitable for an in-situ sustained release application in the human body or in an animal body.

15. A bio-resorbable surgical article, comprising:
    the bio-resorbable polyester according to claim 13.

16. The bio-resorbable surgical article according to claim 15, which is a filament, a rod, a stent or a prostheses.

* * * * *